US008685041B2

(12) United States Patent
Yu et al.

(10) Patent No.: US 8,685,041 B2
(45) Date of Patent: Apr. 1, 2014

(54) NON-INVASIVE ELECTRIC HAIR-TAKING APPARATUS

(75) Inventors: Min Yu, Huaian (CN); Yue Yu, Huaian (CN)

(73) Assignee: Huaian Yumin Hair Planting Clinic, Jiangsu (CN)

( * ) Notice: Subject to any disclaimer, the term of this patent is extended or adjusted under 35 U.S.C. 154(b) by 800 days.

(21) Appl. No.: 12/448,659

(22) PCT Filed: Dec. 22, 2008

(86) PCT No.: PCT/CN2008/002042
§ 371 (c)(1),
(2), (4) Date: Jun. 29, 2009

(87) PCT Pub. No.: WO2009/103198
PCT Pub. Date: Aug. 27, 2009

(65) Prior Publication Data
US 2010/0324571 A1    Dec. 23, 2010

(30) Foreign Application Priority Data

Feb. 20, 2008  (CN) .......................... 2008 1 0020673

(51) Int. Cl.
*A61B 17/50* (2006.01)
(52) U.S. Cl.
USPC ........................................................ 606/133
(58) Field of Classification Search
USPC .............. 600/564–568; 606/36, 42, 131, 133, 606/179, 180, 184
See application file for complete search history.

(56) References Cited

U.S. PATENT DOCUMENTS

| 4,972,825 A | * | 11/1990 | Vescovo, Jr. .................. 600/186 |
| 5,827,297 A | | 10/1998 | Boudjema |
| 2002/0055689 A1 | * | 5/2002 | Kaplan et al. ................. 600/567 |

FOREIGN PATENT DOCUMENTS

| CN | 2676844 Y | 2/2005 |
| CN | 1980608 A | 6/2007 |
| CN | 200948156 Y | 9/2007 |
| CN | 101229073 A | 7/2008 |
| CN | 201171698 Y | 12/2008 |
| JP | 2007229330 A | 9/2007 |

* cited by examiner

*Primary Examiner* — Ashley Fishback
(74) *Attorney, Agent, or Firm* — Hudak, Shunk & Farine Co. LPA

(57) ABSTRACT

The present invention discloses a non-invasive electric hair-taking apparatus comprising a shell (2) and a cover (3) connected with each other by a latch (13) to form a handle (14); a step (15) being arranged at the front end of the handle (14). Said shell (2) is comprised of a front chamber, a middle chamber and a rear chamber; a motor (4) being mounted in the front chamber, a switch (6) being mounted on the wall of the middle chamber, a battery (5) being mounted in the rear chamber. Said motor (4), switch (6) and battery (5) forming a circuit by wiring (8). A hair-taking knife (1) is mounted at the front end of a connector (10) that is mounted on the shaft of the motor (4). Said connector (10) being fixedly positioned at the front end of the handle (14) via a locating ring (11) which is engaged with the step (15).

7 Claims, 4 Drawing Sheets

NON-INVASIVE ELECTRIC HAIR-TAKING APPARATUS

FIELD OF THE INVENTION

The present invention relates to a medical device. Specifically, the present invention relates to a hair-taking apparatus. More specifically, the present invention relates to an electric hair-taking apparatus.

BACKGROUND OF THE PRESENT INVENTION

In the past, the primary technology applied for planting hair is first taking a flap from the occiput posterior position or both temporal of a baldness patient and then transplanting the flap onto the top of forehead or parietooccipital area. It is suffering to the patient due to the stitch scar left in the donor area. Further, blood loss is somewhat severe during operation and the patient is prone to be infected; the operation time is long and recovery also takes long. Currently, a scar-free technology is applied to plant hair for baldness patients in which a hair-taking apparatus is used to take good hair follicles and then transplanting the same in the baldness area. This technology requires no operation and has advantages of being free of stitch scar, mild blood loss, zero infection and quick recovery. Therefore, this technology is less suffering. However, said hair-taking apparatus is manually operated, when taking good hair follicles, a user must hold the handle of the apparatus and insert the hair-taking knife into the scalp of a patient. During the hair-taking process, shaft displacement may occur and thus affect the quality of the hair follicles. Meanwhile, the efficiency of said hair-taking apparatus is relatively low.

SUMMARY OF THE INVENTION

One purpose of the present invention is to provide a non-invasive electric hair-taking apparatus. By using the hair-taking apparatus of this invention, quick and accurate taking of good hair follicles can be achieved. Furthermore, the operation time can be shortened significantly thereby improve efficiency and alleviate sufferings of a patient.

The electric hair-taking apparatus of the present invention comprises a hair-taking knife, a handle, a motor, a switch and a battery, wherein the handle comprises a shell and a cover which is attached with each other via a latch; a step is arranged at the front end of the shell and the cover; said motor, switch and battery are mounted in the chamber of the shell, said chamber of the shell being comprised of a front chamber, a middle chamber and a rear chamber; the motor being mounted in the front chamber, the switch being mounted on the wall of the middle chamber, the battery being mounted in the rear chamber; said motor, switch and the battery form a circuit via wiring; said hair-taking knife is mounted at the front end of a connector that is mounted on the shaft of the motor, and said connector is fixedly positioned at the front end of the handle by a locating ring that is engaged with the step.

In a preferred embodiment of the invention, said connector is fixedly positioned on the handle by a locating ring that is engaged with the step, wherein a seal ring is used for the positioning of the connector.

In another preferred embodiment of the present invention, a locating detent is arranged at the front end of the locating ring for the positioning of the connector.

In yet another preferred embodiment of the present invention, the front end of the connector having a hair-taking knife is positioned at the locating detent of the locating ring via a first shaft washer, the rear end of the connector is positioned on the locating ring via a second shaft washer.

In yet another preferred embodiment of the present invention, a locking block which is engaged with the step is arranged on the location ring.

In yet another preferred embodiment of the present invention, a convex buckler which is engaged with the step is arranged on the seal ring.

In yet another embodiment of the present invention, the hair-taking knife is mounted on the shaft of the motor via a locating detent, the hair-taking knife is fixedly positioned on the shaft of the motor via a fastener nut.

In some embodiments, an ornamental covering is arranged on the handle for handsome appearance.

Said ornamental covering may have an indentation, wherein the switch that is mounted on the shell wall extends above the outside wall of the ornamental covering from the indentation.

In some embodiments of the present invention, the front end of the handle is covered by a protection sleeve.

When installing the hair-taking apparatus of the present invention, the motor is mounted in the front chamber of the shell, the switch is mounted on the wall of the middle chamber of the shell, the battery is mounted in the rear chamber of the shell, the hair-taking knife is mounted on the shaft of the motor via a connector, the shell is attached with the cover via a latch to form the handle, the step at the front end of the handle is used to fixedly position the connector via a seal ring and a locating ring. The outer ornamental covering is assembled on the handle. When using the hair-taking apparatus, a user holds the handle, push the switch to supply power, the motor starts to run and the shaft thereof drives the hair-taking knife to rotate. The hair-taking knife only rotates in the radial direction of the locating detent and thereby a shaft displacement is eliminated. By exert a small downward force on the handle, the hair-taking knife can be inserted into the predetermined area to take good quality hair follicles.

The electric hair-taking apparatus can be applied to replace a manual type to take hair follicles. Said hair-taking apparatus of the present invention is accurate, quick and thus can improve efficiency. In addition, this novel hair-taking apparatus can also improve the success rate of hair planting.

The present invention also discloses another electric hair-taking apparatus. Said hair-taking apparatus comprises a hair-taking knife, a shell, a cover, a motor and a battery, the shell and the cover is attached with each other by a latch to form a chamber; the motor, battery and a switch being mounted in the chamber of the shell, said motor, switch and the battery forming a circuit by wiring; the hair-taking knife is mounted at the front end of a connector. The hair-taking knife of the present invention just moves back and forth alternatively and does not rotate around the axis of the motor.

To achieve the purpose of this invention, a gear is fixedly arranged at the front end of the output shaft of the motor, a face gear having a cam is arranged on an axle which is perpendicular with respect to the output shaft of the motor. Said face gear is arranged to engage with the gear on the output shaft. A ring opening is present at one end of the connector and said ring opening sits around the central rotating axle of the face gear and said cam is in the ring opening; a sleeve is arranged for the connector and the inner diameter of which is adapted to ensure that the connector can move back and forth in the sleeve, while a radial movement with respect to the sleeve is substantially eliminated. On each side of the sleeve a convex is present to fixedly engage with the respective hole arranged in the shell as well as the cover of the hair-taking apparatus.

A DC variable speed motor can be applied to control the speed of the motor.

For handsome appearance, an ornamental covering can be used to cover the shell of the hair-taking apparatus of the present invention.

The present application further discloses another electric hair-taking apparatus. Said hair-taking apparatus comprises a hair-taking knife, a shell, a cover, a motor, a switch and a battery, the shell and the cover is attached with each other by a latch to form a chamber; the motor, battery and the switch is mounted in the chamber, or the wall of the shell, said motor, switch and the battery forms a circuit by wiring. Further, a circuit for controlling the direction of rotation of the motor is arranged on the shell of the hair-taking apparatus. Said hair-taking knife is rotatablely attached to the shell via an axle (hair-taking axle) that is parallel to the output shaft of the motor. Said output shaft additionally has a short axle that is parallel with the central axis of the output shaft. At the end of the hair-taking axle which is adjacent to the output shaft of the motor, a cam is arranged. At the most top of the cam, another short axle is present and parallel to the hair-taking axle. Said two short axles are connected to each other by a connector having two apertures that are adapted to receive the short axles.

For handsome appearance, an ornamental covering can be used to cover the shell of the hair-taking apparatus of the present invention.

DETAILED DESCRIPTION OF THE PRESENT INVENTION

Figure 1:
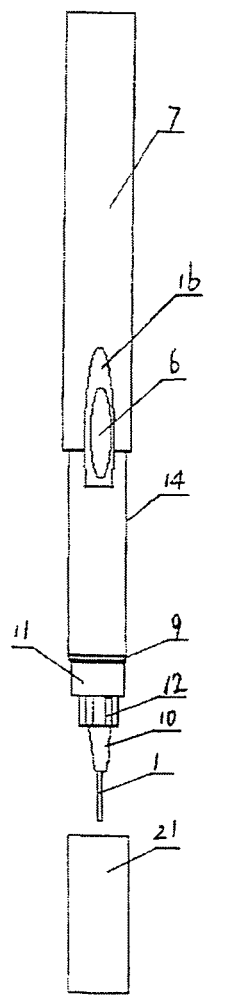
FIG. 1 is a structural diagram of an electric hair-taking apparatus in the present invention.

The present invention will be further described in connection with the accompanying drawings. It should be understood that the specific details shown in the drawings are only used to describe the present invention and would not be construed as any limiting thereto. The scope of the present invention would rather be defined by the claims.

Figure 2:
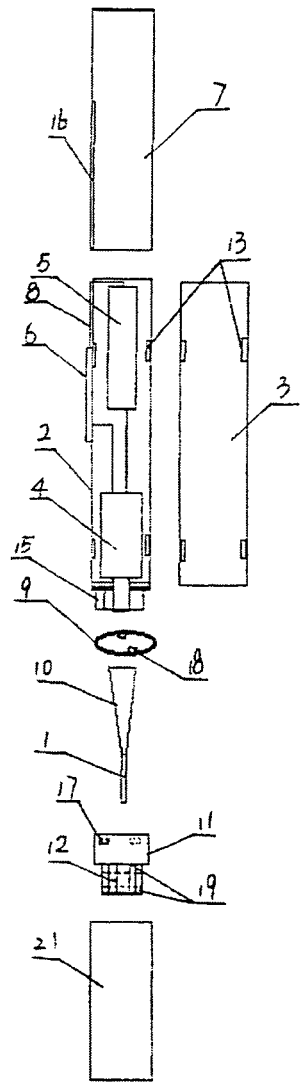
FIG. 2 is an exploded structural diagram of the electric hair-taking apparatus shown in FIG. 1.
Figure 3:
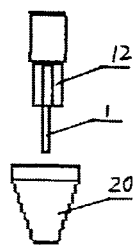
FIG. 3 is an installation schematic diagram of a portion of the electric hair-taking apparatus shown in FIG. 1.

A hair-taking apparatus is shown in FIGS. 1, 2, 3. Said hair-taking apparatus comprises a hair-taking knife 1, a handle 14, a motor 4, a switch 6 and a battery 5. The handle comprises a shell 2 and a cover 3 which is connected with each other by a latch 13 to form a chamber. A step 15 is arranged at the front end of the shell and cover; the motor 4, switch 6 and the battery 5 are mounted in said chamber. Said chamber comprises a front chamber, a middle chamber and a rear chamber; the motor 4 is mounted in the front chamber, the switch 6 is mounted on the wall of the middle chamber, the battery 5 is mounted in the rear chamber; said motor 4, switch 6 and battery 5 forms a circuit by wiring 8; said air-taking knife 1 is mounted at the front end of a connector 10 that is mounted on the shaft of the motor 4, said connector 10 is fixedly positioned at the front end of the handle 14 via a locating ring 11 which is engaged with the step 15.

Additionally, said connector 10 is fixedly positioned on the handle 14 via a locating ring 11 which is engaged with the step 15, a seal ring 9 is used for the positioning of the connector 10.

Additionally, a locating detent 12 is arranged at the front end of the locating ring 11 for the positioning of the connector 10.

Additionally, the front end of the connector 10 having a hair-taking knife 1 is positioned at the locating detent 12 of the locating ring 11 via a first shaft washer 19, the rear end of the connector 10 is positioned on the locating ring 11 via a second shaft washer 19.

Additionally, a locking block 17 which is engaged with the step 15 is arranged on the location ring 11.

Additionally, a convex buckler 18 which is engaged with the step 15 is arranged on the seal ring 9.

As shown in FIG. 3, the hair-taking knife 1 is mounted on the shaft of the motor 4 via the locating detent 12; the hair-taking knife 1 is fixedly positioned on the shaft of the motor 4 via a fastener nut 20.

Additionally, an ornamental covering 7 is arranged on the handle 14.

Said ornamental covering 7 has an indentation 16 and the switch 6 which is mounted on the shell wall extends above the outside wall from the indentation 16.

Additionally, the front end of the handle 14 is covered by a protection sleeve 21.

When installing the hair-taking apparatus of the present invention, the motor 4 is mounted in the front chamber, the switch 6 is mounted on the wall of the middle chamber, the battery 5 is mounted in the rear chamber, the hair-taking knife 1 is mounted on the shaft of the motor via a connector 10, the shell 2 is attached with the cover 3 via the latch 13, the step 15 at the front end of the handle is used to fixedly position the connector 10 via the seal ring 9 and the locating ring 11. The outer ornamental covering 7 is being assembled on the handle 14. When using the hair-taking apparatus, a user holds the handle 14, push to turn on the switch 6 to supply power, the motor 4 starts to run and the shaft thereof drives the hair-taking knife 1 to rotate. The hair-taking knife 1 only rotates in the radial direction of the locating detent 12 and thereby a shaft displacement is eliminated. By exerting a small downward force on the handle 14, the hair-taking knife can be inserted into the predetermined area to take good quality hair follicle.

Figure 4:
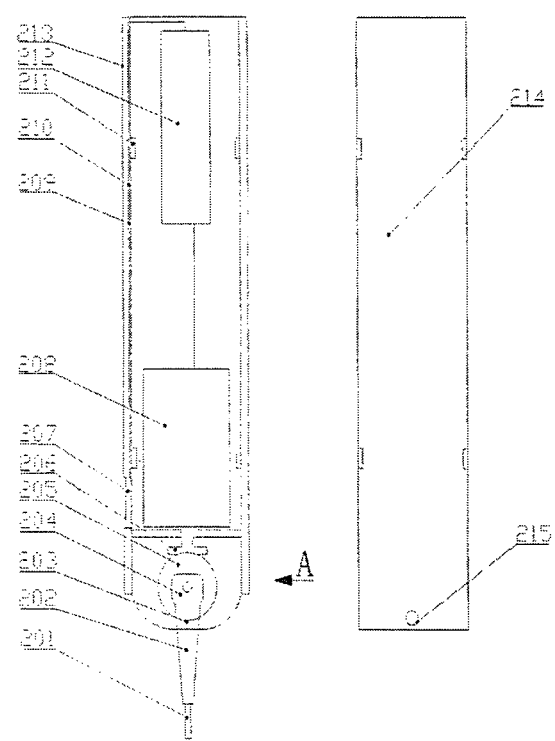
FIG. 4 is a structural diagram of another electric hair-taking apparatus in the present invention.
Figure 5:
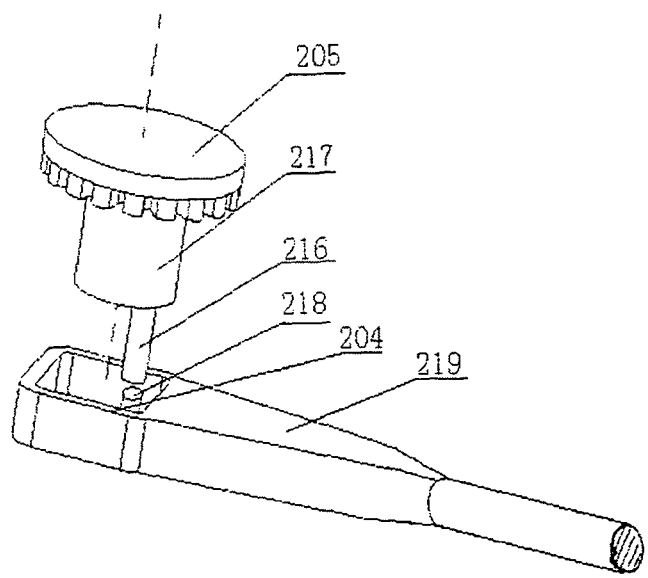
FIG. 5 is an exploded three-dimensional diagram of a portion of the electric hair-taking apparatus shown in FIG. 4 in "A" direction.

FIG. 4 shows a structural diagram of another electric hair-taking apparatus in the present invention. Said hair-taking apparatus comprises a hair-taking knife 201, a shell 210, a cover 214, a motor 208, a switch 207 and a battery 212; the shell 210 and the cover 214 is attached with each other by a latch 211; said motor 208, switch 207 and the battery 212 forms a circuit by wiring which is mounted on the wall of the shell; the hair-taking knife 201 is mounted at the front end of a connector 219. As shown in FIG. 5, to achieve the purpose of this invention, a gear 206 is fixedly arranged at the front end of the output shaft of the motor 208, a face gear 205 having a cam 217 is arranged on an axle 218 which is perpendicular with respect to the output shaft of the motor 208. Said face gear 205 is arranged to engage with the gear 206 on the output shaft. At one end of the connector 219, a ring opening 204 is present and said ring opening 204 sits around the central rotating axle of the face gear 205 having the cam 217 and said cam 217 is located in the ring opening 204; a sleeve is arranged for the connector and the inner diameter of which is adapted to ensure that the connector 219 can only move back and forth in the sleeve, while a radial movement with respect to the sleeve is substantially eliminated. On each side of the sleeve a convex 203 is present to fixedly engage with the respective hole 215 arranged in the shell 210 as well as the cover 214 of the hair-taking apparatus.

When installing the electric hair-taking apparatus as shown in FIG. 4, the battery 212 and the motor 208 are first installed in the chamber of shell 210 and then form a circuit with the switch 207 by wiring. Said shell 210 may be pre-formed as required by using technologies already known, such as but without limitation to integral injection molding. The shell 210 can also be prepared by first forming several individual parts and then attached the same by means known in the art. The gear 206 is fixedly installed on the output shaft of the motor 208. In the adjacent area of the gear 206 on the shell, an axle 218 is fixedly arranged, which will be used for installing the face gear 205. Sitting the ring opening 204 at one end of the connector 219 around the axle 218, and then inserting the axle sleeve 216 for the face gear 205 on the axle 218 and make sure that the cam 217 of the face gear 205 is properly located in the ring opening 204. The face gear 205 so installed is engaged with the gear 206 so that the face gear 205 can be rotated around the axle 218, and the cam 217 of the face gear 205 moves the ring opening 204 back and forth to make the connector having the hair-taking knife at the front end thereof move back and forth but free of rotation. For close contact, a sleeve 202 is arranged on the connector 219 and the inner size of the sleeve makes the connector 219 move therein back and forth and a radial movement with respect to the sleeve is substantially eliminated. At opposite sides of the sleeve 202, a convex 203 is present and said two convexes are engaged with the two holes 215 accordingly which is present in the shell or in the cover (the hole in the shell is not shown in FIG. 4).

Figure 6:
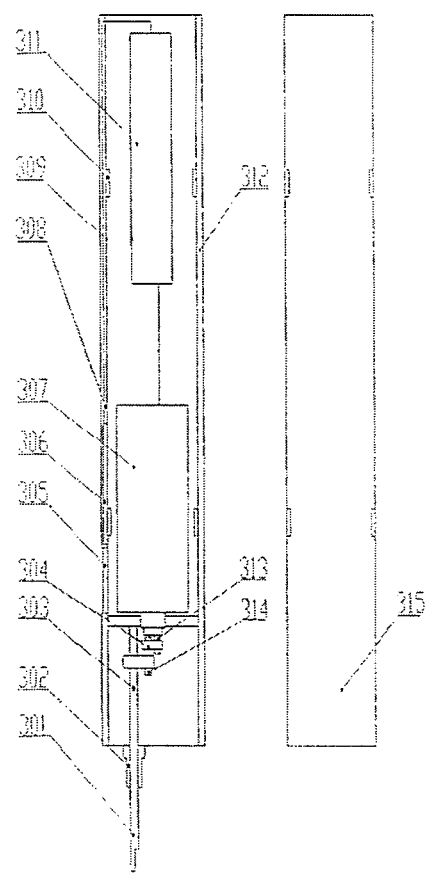
FIG. 6 is a structural diagram of a further electric hair-taking apparatus in the present invention.

FIG. 6 is a structural diagram of a further another electric hair-taking apparatus of the present invention. As shown in FIG. 6, the electric hair-taking apparatus comprises a hair-taking knife 301, a shell 309, a motor 307, a switch 305 and a battery 311, the shell 309 is attached with a cover 315 by a latch; the motor 307, battery 311 and the switch 305 are mounted in the chamber of the shell 309; said motor 307, switch 305 and the battery 311 form a circuit by wiring 308 which is mounted on the wall of the shell 309. Further, a circuit 306 for controlling the direction of rotation of the motor is arranged on the shell 309 of the hair-taking apparatus. Said hair-taking knife 301 is rotatablely attached to the shell via an axle (hair-taking axle 303) that is parallel to the output shaft of the motor 307. Said output shaft additionally has a short axle 313 that is parallel with the central axis of the output shaft. At the end of hair-taking axle which is adjacent to the output shaft of the motor 307, a cam is arranged. At the most top of the cam, another short axle 314 is present and parallel with the hair-taking axle. Said two short axles 313, 314 are connected to each other by a connector 304 having two apertures that are adapted to receive the short axles 313, 314.

The motor 307 starts to run when the circuit is closed. When the hair-taking apparatus is rotated to a predetermined position, it will be locked due to the shape of the cam. By operating the switch 305 of the circuit 306 for controlling the direction of rotation, the direction of rotation of the motor 307 can be changed and thus the hair-taking knife 302 can rotate to the opposite direction for a certain extent. This hair-taking apparatus is easy to operate, more reliable and much safer.

Having described the preferred embodiments of the invention, it is understood that the invention defined by the appended claims is not to be limited by particular details set forth in the above description, as many apparent variations thereof are possible without departing from the spirit or scope thereof.

What is claimed is:

1. A non-invasive electric hair-taking apparatus, comprising:
a hair-taking knife, a shell having a chamber, a cover, a motor, a switch and a battery, the shell and the cover are attached with each other by a latch; the motor, battery and switch being mounted in the chamber of the shell, said motor, switch and battery forming a circuit by wiring; wherein the hair-taking knife is mounted at a front end of a connector; a gear is fixedly arranged at a front end of an output shaft of the motor, wherein the shell has an axle fixed thereto, wherein a face gear having a cam is rotatably arranged on the axle by inserting the axle into an axle sleeve of the face gear, wherein the axle is perpendicular with respect to the output shaft of the motor; said face gear is arranged to engage with the gear on the output shaft; one end of the connector having a ring opening and said ring opening sits around a central rotating axis of the face gear and said cam is located in the ring opening; a sleeve is arranged for the connector and an inner diameter of which is adapted to ensure that the connector can move back and forth therein, on each side of the sleeve a convex element is present to fixedly engage with a respective hole arranged in the shell as well as the cover of the hair-taking apparatus.

2. The non-invasive electric hair-taking apparatus according to claim 1, wherein said motor is a DC variable speed motor.

3. The non-invasive electric hair-taking apparatus according to claim 1, further comprises an ornamental covering.

4. A non-invasive electric hair-taking apparatus, comprising: a hair-taking knife, a shell having a chamber, a cover, a motor, a switch and a battery, the shell and the cover are attached with each other; the motor, battery and switch being mounted in the chamber of the shell, said motor, switch and battery forming a circuit by wiring;
wherein the hair-taking knife is mounted at a front end of a connector; wherein a gear is fixedly arranged at a front end of an output shaft of the motor, wherein the shell has an axle fixed thereto, wherein the apparatus includes a face gear arranged to engage with the gear on the output shaft, wherein the face gear has a cam and an axle sleeve, wherein one end of the connector has a ring opening and said ring opening sits around a central rotating axis of the face gear and said cam is located in the ring opening, wherein the axle sleeve is inserted on the axle of the shell such that the face gear can be rotated around the axle and the cam moves the ring opening of the connector back and forth to make the connector having the hair-taking knife at a front end thereof move back and forth but free of rotation.

5. The non-invasive electric hair-taking apparatus according to claim 4, wherein said motor is a DC variable speed motor 6. The non-invasive electric hair-taking apparatus according to claim 4, further comprises an ornamental covering.

7. The non-invasive electric hair-taking apparatus according to claim 4, wherein a sleeve is arranged on the connector and an inner size of the sleeve makes the connector move therein back and forth and a radial movement of the connector with respect to the sleeve is substantial eliminated.

* * * * *